United States Patent
Nasu et al.

(10) Patent No.: US 11,572,484 B2
(45) Date of Patent: Feb. 7, 2023

(54) INK-JET INK COMPOSITION, INK-JET CARTRIDGE, AND DECORATION DEVICE

(71) Applicant: SHISEIDO COMPANY, LTD., Tokyo (JP)

(72) Inventors: Akio Nasu, Yokohama (JP); Tomoyuki Katsuyama, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 352 days.

(21) Appl. No.: 16/642,409

(22) PCT Filed: Jul. 18, 2018

(86) PCT No.: PCT/JP2018/026891
§ 371 (c)(1),
(2) Date: Feb. 27, 2020

(87) PCT Pub. No.: WO2019/044229
PCT Pub. Date: Mar. 7, 2019

(65) Prior Publication Data
US 2021/0155816 A1    May 27, 2021

(30) Foreign Application Priority Data

Sep. 1, 2017   (JP) ................. 2017-168390

(51) Int. Cl.
*C09D 11/38*   (2014.01)
*A45D 34/04*   (2006.01)
(Continued)

(52) U.S. Cl.
CPC .............. *C09D 11/38* (2013.01); *A45D 34/04* (2013.01); *A61K 8/025* (2013.01); *A61K 8/27* (2013.01);
(Continued)

(58) Field of Classification Search
CPC ....... C09D 11/322; C09D 11/40; C09D 11/38; C09D 11/54; A61K 2800/43;
(Continued)

(56) References Cited

U.S. PATENT DOCUMENTS

2002/0041854 A1* 4/2002 Hadasch .................. A61Q 1/12
424/63
2003/0100646 A1* 5/2003 Anchor .................. C09D 5/033
524/323
(Continued)

FOREIGN PATENT DOCUMENTS

JP   2006-321967    11/2006
JP   2007-136812    6/2007
(Continued)

OTHER PUBLICATIONS

PCT/JP2018/026891, International Search Report and Written Opinion dated Nov. 9, 2018, 9 pages—Japanese, 6 pages—English.

*Primary Examiner* — John Zimmermann
(74) *Attorney, Agent, or Firm* — Andrew F. Young; Nolte Lackenbach Siegel

(57) ABSTRACT

An ink-jet ink composition includes: a solvent; a pigment comprising a first powder, the surface of which, in the solvent, bears a first charge; an ionic polymer having a second charge, which is counter to the first charge; and polyvalent ions having the first charge. The ink composition has a surface tension of 53 mN/m or less.

11 Claims, 3 Drawing Sheets

(51) Int. Cl.
  *A61K 8/02*  (2006.01)
  *A61K 8/27*  (2006.01)
  *A61K 8/29*  (2006.01)
  *A61K 8/81*  (2006.01)
  *A61Q 1/02*  (2006.01)
  *B41J 2/05*  (2006.01)
  *B41J 2/175*  (2006.01)
  *C09D 11/322*  (2014.01)
  *A45D 34/00*  (2006.01)

(52) U.S. Cl.
  CPC .............. *A61K 8/29* (2013.01); *A61K 8/8152* (2013.01); *A61Q 1/02* (2013.01); *B41J 2/05* (2013.01); *B41J 2/17503* (2013.01); *C09D 11/322* (2013.01); *A45D 2034/005* (2013.01); *A61K 2800/5424* (2013.01); *A61K 2800/87* (2013.01)

(58) Field of Classification Search
  CPC . A61K 2800/5424; A61K 8/29; B41J 2/2114; B41J 2/2107
  See application file for complete search history.

(56) References Cited

U.S. PATENT DOCUMENTS

| | | | |
|---|---|---|---|
| 2004/0196351 A1* | 10/2004 | Kida | B41M 7/0027 |
| | | | 347/105 |
| 2008/0317963 A1* | 12/2008 | Barcock | D21H 23/48 |
| | | | 427/420 |
| 2011/0001779 A1* | 1/2011 | Kida | B41J 2/515 |
| | | | 347/42 |
| 2014/0118449 A1 | 5/2014 | Sarkisian et al. | |
| 2015/0114246 A1* | 4/2015 | Chopra | C08K 5/45 |
| | | | 101/483 |
| 2015/0115202 A1 | 4/2015 | Kagata | |
| 2017/0156994 A1* | 6/2017 | Lingoes | A61K 8/86 |

FOREIGN PATENT DOCUMENTS

| | | |
|---|---|---|
| JP | 2008-266527 | 11/2008 |
| JP | 2009-509005 | 3/2009 |
| JP | 2011-194879 | 10/2011 |
| JP | 2014-185236 | 10/2014 |
| JP | 2015-083628 | 4/2015 |
| JP | 2015-0118449 | 4/2015 |
| JP | 2016-190930 | 11/2016 |
| JP | 2016-216676 | 12/2016 |
| JP | 2017-039922 | 2/2017 |

\* cited by examiner

INK-JET INK COMPOSITION, INK-JET CARTRIDGE, AND DECORATION DEVICE

CROSS REFERENCE TO RELATED APPLICATIONS

The present invention is based upon and claims the benefit of PCT/JP2018/26891 filed Jul. 18, 2018 the entire contents of which are incorporated herein by reference and also claims the priority of Japanese Patent Application No. 2017-168390 (filed on Sep. 1, 2017), the disclosure of which is incorporated herein in its entirety by reference.
FIGURE SELECTED FOR PUBLICATION
FIG. 1.

TECHNICAL FIELD

The present disclosure relates to an ink composition for ink-jet applications. Further, the present disclosure relates to an ink-jet cartridge comprising the ink composition. Furthermore, the present disclosure relates to a cosmetic device comprising the ink-jet cartridge.

BACKGROUND ART

In general, pigments (powders) are added to inks applied to ink-jet printers. When pigments in inks aggregate or sediment, inks may not be dispensed or a usable term of ink cartridges may be shortened. Accordingly, an aqueous ink for ink-jet recordings that is aimed to enhance redispersibility of titanium oxide used as the pigment is proposed in Patent Literature 1, for example.

Patent Literature 1 discloses an aqueous ink for ink-jet recording comprising titanium oxide (A) and a pigment dispersing agent (B). In the aqueous ink for ink-jet recording, the pigment dispersing agent (B) has a constituting unit derived from an anionic group-containing monomer (a) and a constituting unit derived from polyalkylene glycol (meth) acrylate (b); an average number of moles added of alkylene oxide of the polyalkylene glycol (meth)acrylate (b) is 15 or greater and 100 or smaller; an acid value of the pigment dispersing agent (B) is 100 mgKOH/g or greater and 400 mgKOH/g or smaller; and the content of the pigment dispersing agent (B) is 0.3 part by mass or greater and 18 parts by mass or smaller with respect to 100 parts by mass of titanium oxide (A).

Patent Literature 2 discloses an ink-jet cartridge comprising an absorber for storing an ink in an ink tank.

CITATION LIST

Patent Literature

Patent Literature 1: Japanese Unexamined Patent Publication No. 2017-39922A.
Patent Literature 2: Japanese Unexamined Patent Publication No. 2011-194879A

SUMMARY OF INVENTION

Technical Problem

Inks applied to ink-jet applications are demanded to be low in viscosity in order to be make it possible to dispense ink as fine droplets: however, when inks are low in viscosity, pigment powder easily sediments. When pigment powder sediments, continuation of uniform dispensing of ink becomes difficult. Furthermore, when pigment sediments, powder pigment aggregates and may easily become impossible to be dispensed. Therefore, an ink composition in which sedimentation or aggregation of pigment powder hardly occurs is desired.

As described in Patent Literature 2, there are ink-jet cartridges that comprise fibrous absorbers for storing inks. When the aqueous ink for ink-jet recording as described in Patent Literature 1 is stored in such absorber, redispersion is not easy when the pigment powder sediments in the absorber, and thus problems as stated above may arise too. Therefore, an ink composition that can be uniformly and stably dispensed is also demanded in an ink cartridge comprising such an absorber.

Solution to Problem

According to a first aspect of the present disclosure, an ink composition for ink-jet application is provided, the ink composition comprising a solvent, a pigment comprising a first powder bearing a first charge on a surface thereof in the solvent, an ionic polymer bearing a second charge that is opposite to the first charge, and a polyvalent ion bearing the first charge. A surface-tension of the ink composition is 53 mN/m or smaller.

According to a second aspect of the present disclosure, an ink-jet cartridge is provided, the ink-jet cartridge comprising the ink composition according to the first aspect.

According to a third aspect of the present disclosure, a cosmetic device is provided, the cosmetic device comprising the ink-jet cartridge according to the second aspect, which is detachable, the cosmetic device dispensing the ink composition to skin.

Advantageous Effects of Invention

In the ink composition of the present disclosure, sedimentation and aggregation of pigment are suppressed. Accordingly, the ink composition can be applied as an ink for ink-jet applications even when pigment which is easy to sediment and/or aggregate is used.

DESCRIPTION OF EMBODIMENTS

Figure 1:
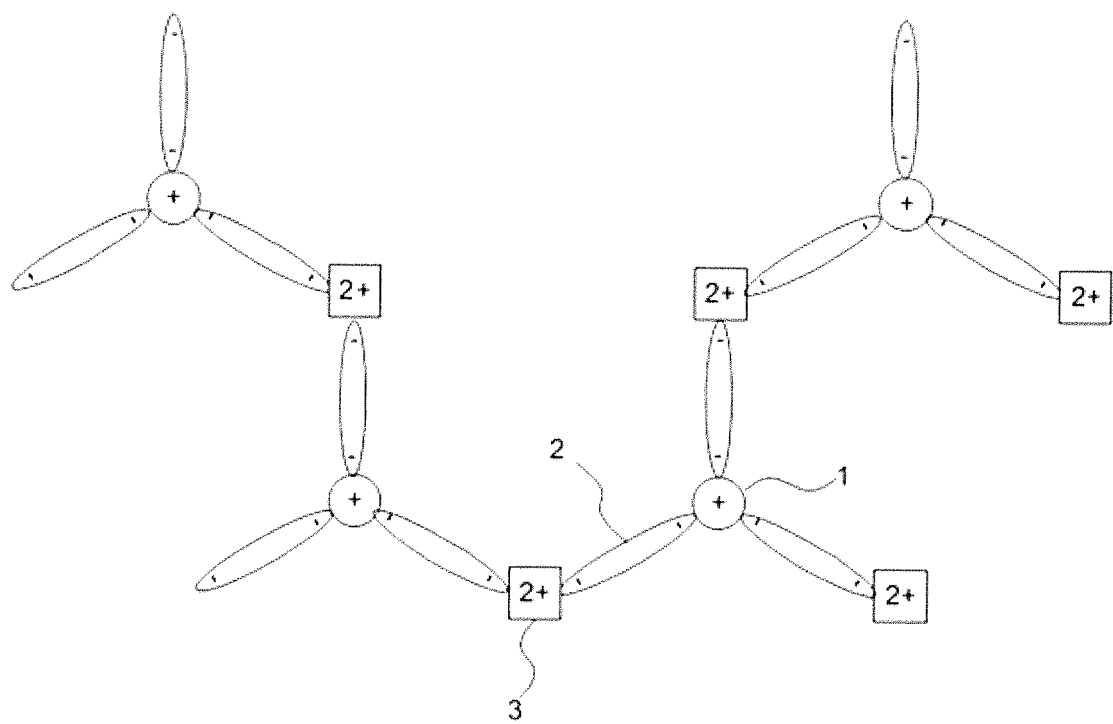
FIG. 1 is a schematic view for describing a dispersed state of pigment.

Preferred modes of the aforementioned aspects are described below.

According to a preferred mode of the above first aspect, a shape of the first powder is mainly spherical.

According to a preferred mode of the above first aspect, the first powder has an average particle size of 150 nm to 350 nm.

According to a preferred mode of the above first aspect, a primary particle of the first powder is spherical.

According to a preferred mode of the above first aspect, the primary particle of the first powder has an average particle size of 100 nm to 300 nm.

According to a preferred mode of the above first aspect, a ratio of the first powder with respect to the total amount of the pigment is 40% by mass or greater.

According to a preferred mode of the above first aspect, the pigment further comprises a second powder that is different from the first powder.

According to a preferred mode of the above first aspect, the second powder has an average particle size of 50 nm to 300 nm.

According to a preferred mode of the above first aspect, the content of the first powder in the pigment is 45% by mass to 90% by mass with respect to the total amount of the pigment. The content of the second powder in the pigment is 10% by mass to 55% by mass with respect to the total amount of the pigment.

According to a preferred mode of the above first aspect, the first powder is titanium dioxide. The second powder is zinc oxide.

According to a preferred mode of the above first aspect, the content of the pigment is 5% by mass to 25% by mass with respect to the mass of the ink composition.

According to a preferred mode of the above first aspect, the viscosity at a shear velocity of 100 $s^{-1}$ or greater is 40 mPa·s or smaller.

According to a preferred mode of the above first aspect, the ink composition further comprises a surface-tension lowering agent for lowering the surface-tension of the ink composition.

According to a preferred mode of the above first aspect, the surface-tension lowering agent is at least either one of a polyhydric alcohol and a surfactant.

According to a preferred mode of the above first aspect, the pigment and the ionic polymer are electrostatically and/or ionically bonded with one another. The ionic polymer and the polyvalent ion are electrostatically and/or ionically bonded with one another.

According to a preferred mode of the above first aspect, the pigment forms a weak flocculation via the ionic polymer and the polyvalent ion.

According to a preferred mode of the above first aspect, the first charge is a positive charge. The ionic polymer has an anionic functional group.

According to a preferred mode of the above first aspect, the ionic polymer comprises at least either one of a polyacrylate ion and a hexamethaphosphate ion.

According to a preferred mode of the above first aspect, the content of a polyelectrolyte that is a source of the ionic polymer is 0.01 part by mass to 0.2 part by mass with respect to 1 part by mass of the pigment.

According to a preferred mode of the above first aspect, the polyvalent ion comprises at least either one of a magnesium ion and a calcium ion.

According to a preferred mode of the above first aspect, the content of a salt that is a source of the polyvalent ion is 0.15 part by mass to 2 parts by mass with respect to 1 part by mass of the polyelectrolyte that is the source of the ionic polymer.

According to a preferred mode of the above first aspect, the ink composition is applied to an ink-jet application of thermal dispensing type.

According to a preferred mode of the above first aspect, the solvent comprises water.

According to a preferred mode of the above first aspect, the ink composition is applied to skin.

According to a preferred mode of the above second aspect, the ink-jet cartridge further comprises an ink absorber that absorbs and stores an ink. At least a part of the ink composition is stored in the absorber.

According to a preferred mode of the above second aspect, a method of dispensing droplets in ink-jet applications is a thermal method.

An ink composition of the present disclosure according to a first embodiment is described.

In the following description, POE is an abbreviation of polyoxyethylene, and POP is an abbreviation of polyoxypropylene. The number in parentheses after POE or POP indicates the average number of moles of POE groups or POP groups added in the compound in question.

In the following description, the reference symbols in the drawings are made for understanding the invention and are not intended to limit the invention to the illustrated embodiments. Moreover, illustrated shapes, dimensions, scales and the like do not limit the invention to the embodiments shown in the drawings. Same elements are shown with the same reference symbols in each embodiment.

The ink composition of the present disclosure comprises a solvent, a pigment, an ionic polymer, and a polyvalent ion.

[Solvent]

The solvent is preferably a liquid that can dissolve an ionic polymer and a metal salt that dissociates a polyvalent ion. The solvent is preferably a polar solvent such that it can dissolve an ionic substance, and more preferably an aqueous solvent. Examples of an aqueous solvent may include water, alcohol, or a mixture thereof.

Examples of the lower alcohol may include ethanol, propanol, isopropanol, isobutyl alcohol, t-butyl alcohol, and the like.

Examples of the polyhydric alcohol may include dihydric alcohol (such as ethylene glycol, propylen glycol, trimethylene glycol, 1,2-butylene glycol, 1,3-butylene glycol, tetramethylene glycol, 2,3-butylene glycol, pentamethylene glycol, 2-butene-1,4-diol, hexylene glycol, octylene glycol, etc); trihydric alcohol (such as glycerin, trimethylolpropane, etc); tetrahydric alcohol (such as such as pentaerythritol such as 1,2,6-hexanetriol, etc); pentahydric alcohol (such as xylitol, etc); hexahydric alcohol (such as sorbitol, mannitol, etc); polyhydric alcohol polymer (such as diethylene glycol, dipropylene glycol, triethylene glycol, polypropylene glycol, tetraethylene glycol, diglycerin, polyethylene glycol, triglycerin, tetraglycerin, polyglycerin, etc); dihydric alcohol alkyl ethers (such as ethylene glycol monomethyl ether, ethylene glycol monoethyl ether, ethylene glycol monobutyl ether, ethylene glycol monphenyl ether, ethylene glycol monohexyl ether, ethylene glycol mono2-methylhexyl ether, ethylene glycol isoamyl ether, ethylene glycol benzil ether, ethylene glycol isopropyl ether, ethylene glycol dimethyl ether, ethylene glycol diethyl ether, ethylene glycol dibutyl ether, etc); dihydric alcohol alkyl ethers (such as diethylene glycol monomethyl ether, diethylene glycol monoethyl ether, diethylene glycol monombutyl ether, diethylene glycol dimethyl ether, diethylene glycol diethyl ether, diethylene glycol butyl ether, diethylene glycol methylethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, dipropylene glycol butyl ether, etc); dihydric alcohol ether ethers (such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disaccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, propylene glycol monophenyl ether acetate, etc); glycerin monoalkyl ether (such as chimyl alcohol, selachyl alcohol, batyl alcohol, etc); sugar alcohol (such as sorbitol, maltitol, maltotriose, mannitol, sucrose, erythritol, glucose, fructose, starch sugar, maltose, xylitol, starch sugar hydrogenated alcohol, etc); glycolide, tetrahydrofurfuryl alcohol; POE-tetrahydrofurfuryl alcohol; POP/POE-butyl ether; tripolyoxypropylene glycerin ether; POP-glycerin ether; POP-glycerin ether phosphoric acid; POP/POE-pentaerythritol ether; polyglycerin, and the like.

[Pigment]

The pigment comprises a first powder. The pigment can further comprise a second powder of a different type from the first powder. It is considered that since types of the first powder and the second powder are different, affinity of the both powders can be lowered and aggregation can be suppressed. The first powder and the second powder are preferably not soluble in the solvent.

In the solvent, the first powder and the second powder bear a first charge on their surfaces. The first charge may be a charge charged by a charging treatment agent. The first charge may be a positive charge, or a negative charge. Analysis and evaluation of the powder bearing the first charge can be performed by measurements of an isoelectric point, pH and the like. Examples of the powder bearing a positive charge on the surface may include zinc oxide, titanium oxide, alumina, and the like. Examples of the powder bearing a negative charge on the surface may include silica and the like. For example, zinc oxide and titanium oxide can be used as a white-based pigment.

The average particle size of the powder in the present disclosure is an average particle size of particles dispersed in the ink composition, unless otherwise specified. When a secondary particle in which primary particles aggregates is present in the ink composition, the average particle size as used in the present disclosure is an average particle size of particles including the primary particle and the secondary particle in which the primary particles aggregates, unless otherwise specified. The average particle size of the powder can be measured in accordance with a dynamic light scattering method.

The shape of the particle in the present disclosure is a shape of a particle dispersed in the ink composition, unless otherwise specified. When a secondary particle in which primary particles aggregates is present in the ink composition, the shape of the particle as used in the present disclosure is a shape of particles including the primary particle and the secondary particle in which the primary particles aggregates, unless otherwise specified.

The average particle size of the first powder is preferably 100 nm or greater, more preferably 150 nm or greater, and furthermore preferably 200 nm or greater, for example. When the average particle size of the first powder is smaller than 100 nm, concealing ability may become too low. Furthermore, the average particle size of the first powder is preferably 350 nm or smaller, and more preferably 300 nm or smaller, for example. When the average particle size of the first powder exceeds 350 nm, sedimentation may easily occur and thus dispensability may deteriorate.

It is preferred that aggregation of particles occurs less is in the first powder. That is, the difference between the average particle size of the first powder and the average particle size of the primary particles of the first powder is preferably small. The average particle size of the primary particles in the first powder is 100 nm or greater, or preferably 150 nm or greater, for example. The average particle size of the primary particles in the first powder is preferably 350 nm or smaller, 300 nm or smaller, or 250 nm or smaller, for example.

It is preferred that the shape of the particles in the first powder is mainly spherical. "Spherical" may mean that, for example, the particles are generally spherical when the powder is observed with a microscope. Dispensability can be enhanced when the first powder has a spherical shape.

The average particle size of the second powder is preferably 50 nm or greater, more preferably 80 nm or greater, and furthermore preferably 100 nm or greater. The average particle size of the second powder is preferably 350 nm or smaller, more preferably 300 nm or smaller, more preferably 250 nm or smaller, and furthermore preferably 200 nm or smaller. If the average particle size is in such sizes, dispensability and concealing ability can be enhanced.

The average particle size of the particles in the second powder can be 10 nm or greater, 20 nm or greater, or 30 nm or greater, for example. The average particle size of the particles in the second powder can be 80 nm or smaller, 70 nm or smaller, or 60 nm or smaller, for example.

The pigment may further comprise other powders. Examples of the powder applicable to the pigment may include inorganic powder (such as talc, kaolin, mica, sericite, muscovite, phlogopite, synthetic mica, lepidolite, biotite, vermiculite, magnesium carbonate, calcium carbonate, aluminum silicate, barium silicate, calcium silicate, magnesium silicate, strontium silicate, tungstate, magnesium, silica, zeolite, glass, barium sulfate, calcined calcium sulfate (calcined gypsum), calcium phosphate, fluorine apatite, hydroxyapatite, ceramic powder, metallic soap (such as zinc myristate, calcium palimitate, and aluminum stearate), and boron nitride, etc); organic powder (such as polyamide resin powder (nylon powder), polyethylene powder, polymethylmethacrylate powder, polystyrene powder, styrene-acrylic acid copolymer powder, benzoguanamine resin powder, poly(tetrafluroethylene) powder, and cellulose powder, silicone resin powder, silk powder, wool powder, urethane powder, etc); inorganic white family pigment (such as titanium dioxide, zinc oxide, etc); inorganic red family pigment (such as iron oxide (colcothar), iron titanate, etc); inorganic brown family pigment (such as γ-iron oxide, etc); inorganic yellow family pigment (such as yellow iron oxide, loess, etc); inorganic black family pigment (such as black iron oxide, carbon black, lower titanium oxide, etc); inorganic purple family pigment (such as manganese violet, cobalt violet, etc); inorganic green family pigment (such as chrome oxide, chrome hydroxide, cobalt titanate, etc); inorganic blue family pigment (such as ultramarine, iron blue, etc); pearl pigment (such as titanium oxide coated mica, titanium oxide coated bismuth oxychloride, titanium oxide coated talc, colored titanium oxide coated mica, bismuth oxychloride, argentine, etc); metal powder pigment (such as aluminum powder, copper powder, etc); organic pigment such as zirconium, barium, or aluminum lake (such as organic pigment such as Red No. 201, Red No. 202, Red No. 204, Red No. 205, Red No. 220, Red No. 226, Red No. 228, Red No. 405, Red No. 201, Orange No. 203, Orange No. 204, Yellow No. 205, Yellow No. 401, Blue No. 401, Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, and Blue No. 1, etc); natural pigment (such as chlorophyll, β-carotene, etc) and the like.

The content of the pigment is preferably 5% by mass or greater, and more preferably 10% by mass or greater with respect to the mass of the ink composition. If the content of the pigment is smaller than 5% by mass, concealing ability may become too low. The content of the pigment can be 15% by mass or greater with respect to the mass of the ink composition, for example. The content of the pigment is preferably 25% by mass or smaller, and more preferably 20% by mass or smaller with respect to the mass of the ink composition. If the content of the pigment exceeds 25% by mass, aggregation easily occurs and thus ink-jet dispensability may deteriorate.

The ratio of the first powder in the pigment is preferably 40% by mass or greater, more preferably 45% by mass or greater, and furthermore preferably 50% by mass or greater with respect to the total amount of the pigment. If the ratio of the first powder in the pigment is smaller than 45% by mass, dispensability may deteriorate. The ratio of the first powder can be the pigment is 55% by mass or greater, 60% by mass or greater, 70% by mass or greater, 80% by mass or greater, 90% by mass or greater, or 100% by mass with respect to the total amount of the pigment, for example. The ratio of the first powder in the pigment can be 95% by mass or smaller, 90% by mass or smaller, 85% by mass or smaller, 80% by mass or smaller, 75% by mass or smaller, or 70% by mass or smaller with respect to the total amount of the pigment, for example.

The ratio of the second powder in the pigment is preferably 10% by mass or greater, 15% by mass or greater, 20% by mass or greater, 25% by mass or greater, or 30% by mass or greater with respect to the total amount of the pigment, for example. By blending the second powder, aggregation of the first powder can be suppressed and, at the same time, concealing ability can be enhanced. The ratio of the second powder in the pigment is preferably 55% by mass or smaller, and more preferably 50% by mass or smaller with respect to the total amount of the pigment, for example. If the ratio of the second powder in the pigment exceeds 55% by mass, aggregation of the pigment easily occurs. The ratio of the second powder in the pigment can be 45% by mass or smaller, 40% by mass or smaller, 35% by mass or smaller, 30% by mass or smaller, 25% by mass or smaller, or 20% by mass or smaller with respect to the total amount of the pigment, for example.

The average particle size of the pigment is preferably 300 μm or smaller. The pigment powder having the average particle size of 300 μm or smaller is preferably 70% by mass or greater, more preferably 80% by mass or greater, more preferably 85% by mass or greater, more preferably 90% by mass or greater, more preferably 95% by mass or greater, and further more preferably 100% by mass with respect to the total amount of the pigment.

Either one of the first powder and the second powder can be titanium dioxide, and the other can be zinc oxide, for example. The first powder can be titanium oxide, and the second powder can be zinc oxide, for example.

[Ionic Polymer]

The ionic polymer may be a polymer that becomes an ion in the solvent. Positive/negative of the charge of the ionic polymer is preferably determined in accordance with the electrification potential of the pigment. One ionic polymer can have one or more ionic functional group(s). Valence of the ionic polymer may be monovalent or polyvalent. The ionic polymer can be added in a form of a polyelectrolyte. The polyelectrolyte can be in a form of an acid or a base.

The ionic polymer bears a second charge opposite to the first charge by electrolytic dissociation in the solvent. In a constituent or a substituent of a polymer chain, the ionic polymer has one or more of an ionic functional group that ionizes in the solvent and has the second charge. Valence of one functional group is preferably lower than that of the polyvalent ion. In order to electrostatically and/or ionically bond a plurality of the ionic polymers to the polyvalent ion, valence of one functional group is more preferably monovalent.

Examples of anionic functional groups of the ionic polymers may include carboxylic acid, sulfurous acid, sulfuric acid, acrylic acid, and salts thereof. Examples of cationic functional groups of the ionic polymers may include amine salt, imine salt and the like.

Examples of anionic ionic polymers may include polyacrylate, hexamethaphosphate, polycarboxylate (a polymer of carboxylate monomer) and the like. Examples of canionic ionic polymers may include polymers having a quaternary ammonium group and the like.

The molecular weight of the ionic polymer is preferably 3,000 or greater, more preferably 5,000 or greater, and further more preferably 6,000 or greater. If the molecular weight is smaller than 3,000, weak flocculation of the pigment cannot be formed. The molecular weight of the ionic polymer is preferably 15,000 or smaller, more preferably 12,000 or smaller, and further more preferably 10,000 or smaller. If the molecular weight exceeds 15,000, dispensability will deteriorate.

The content of the salt (polyelectrolyte) that is a source of the ionic polymer in the ink composition is preferably 0.01 part by mass or greater, and more preferably 0.015 part by mass or greater with respect to 1 part by mass of the pigment. If the content of the polyelectrolyte is smaller than 0.01 part by mass, dispersibility of the pigment will deteriorate. The content of the salt (polyelectrolyte) that is a source of the ionic polymer is preferably 0.2 part by mass or smaller, more preferably 0.1 part by mass or smaller, and further more preferably 0.05 part by mass or smaller with resect to 1 part by mass of the pigment. If the content of the polyelectrolyte exceeds 0.2 part by mass, dispensability will be adversely affected.

[Polyvalent Ion]

A polyvalent ion is an ion bearing the first charge in the solvent. The polyvalent ion is preferably an ion having valence of two or greater.

The polyvalent ion may be a metal ion, for example. Examples of the polyvalent ion as a cation may include metal ions of aluminum, magnesium, calcium, manganese, barium, nickel, iron, zinc, copper, bismuth, tin, silver and the like. Examples of the polyvalent ion as an anion may include sulfate ion, carbonate ion and the like. Among them, magnesium ion and calcium ion are preferred in particular in terms of safety.

In cases where the polyvalent ion is a metal ion, the polyvalent ion can be added in a form as a metal salt. The metal salt may be one that ionizes (dissolves) in the solvent. Examples of the metal salt may include metal salts such as chloride salt, hydroxide salt, nitrate, sulfate, phosphate, acetate, carbonate and the like. These metal salts can be used alone or by combining two or more types thereof.

The content of the salt that is a source of the polyvalent ion in the ink composition of the present disclosure is preferably 0.05 part by mass or greater, and more preferably 0.1 part by mass or greater with respect to 1 part by mass of the polyelectrolyte that is a source of the ionic polymer. If the content of the salt is smaller than 0.05 part by mass, effect for enhancing dispersibility of the pigment cannot be achieved. For example, the content of the salt can be 0.2 part by mass or greater, 0.3 part by mass or greater, 0.4 part by mass or greater, or 0.5 part by mass or greater with respect to 1 part by mass of the polyelectrolyte. The content of the salt that is a source of the polyvalent ion is preferably 2 parts by mass or smaller, and more preferably 1 part by mass or smaller with respect to 1 part by mass of the polyelectrolyte that is a source of the ionic polymer. If the content of the salt exceeds 2 parts by mass, dispensability will be affected. For example, the content of the salt can be 1.5 parts by mass or smaller, 1 part by mass or smaller, 0.7 part by mass or smaller, 0.5 part by mass or smaller, or 0.4 part by mass or smaller with respect to 1 part by mass of the polyelectrolyte.

[Electrifying Agent]

The ink composition of the present disclosure may comprise an electrifying agent (charging agent) that charges the surface of the pigment with the first charge when the pigment is not charged in the solvent. Cationic polymers such as polyethylene imine and the like, for example, may be used as the electrifying agent to positively charge the surface of the pigment. Anionic polymers such as polyacrylate and the like, for example, may be used as the electrifying agent to negatively charge the surface of the pigment.

[Surface-Tension Lowering Agent]

The ink composition of the present disclosure may further comprise a surface-tension lowering agent for lowering the surface-tension of the ink composition. For example, alcohols, surfactants and the like may be used as the surface-tension lowering agent. The lower alcohols and polyvalent alcohols listed above may be used as the alcohol. Anionic surfactants, cationic surfactants, amphoteric surfactants, and nonionic surfactants listed below may be used as the surfactant.

Examples of the anionic surfactants that may be used may include fatty acid soap (such as sodium laurate, and sodium palmitate); higher alkyl sulfate ester salt (such as sodium lauryl sulfate, and potassium lauryl sulfate); alkyl ether sulfate ester salt (such as POE-lauryl sulfate triethanolamine, and sodium POE-lauryl sulfate); N-acyl sarcosinic acid (such as sodium lauroyl sarcocinate); higher fatty acid amide sulfonate (such as sodium N-stearoyl-N-methyltaurate, sodium N-myristoyl-N-methyltaurate, sodium methyl cocoyl taurate, and sodium laurylmethyl taurate); phosphate ester salt (sodium POE-oleylether phosphate, POE-stearylether phosphate, potassium cetyl phosphate); sulfosuccinate (such as sodium di-2-ethylhexyl sulfosuccinate, sodium monolauroyl monoethanolamide polyethylene sulfosuccinate, and sodium lauryl polypropylene glycol sulfosuccinate); alkylbenzene sulfonate (such as sodium linear dodecylbenzene sulfonate, triethanolamine linear dodeylbenzene sulfonate, and linear dodecylbenzene sulfonate); higher fatty acid ester sulfate ester salt (such as sodium hydrogenated gryceryl cocoate sulfate); N-acyl glutamate (such as monosodium N-lauroyl glutamate, disodium N-stearoyl glutamate, and monosodium N-myristoyl-L-glutamate); sulfonated oil (such as Turkey red oil); POE-alkyl ether carboxylic acid; POE-alkyl aryl ether carboxylate; α-olefine sulfonate; higher fatty acid ester sulfonate; secondary alcohol sulfate ester salt; higher fatty acid alkylolamide sulfate ester salt; sodium lauroyl monoethanolamide succinate; N-palmitoyl asparaginate ditriethanolamine; sodium casein; and the like.

Examples of the cationic surfactants may include alkyltrimethyl ammonium salt (such as stearyltrimethyl ammonium chloride, lauryltrimethyl ammonium chloride); alkylpyridinium salt (such as cetylpyridinium chloride); dialkyldimethyl ammonium salt (such as distearyldimethyl ammonium chloride); poly (N,N'-dimethyl-3,5-methylenepiperidinium) chloride; alkyl quaternary ammonium salt; alkyldimethylbenzyl ammonium salt; alkylisoquinolinium salt; dialkylmorphonium salt; POE alkylamine; alkylamine salt; polyamine fatty acid derivative; amyl alcohol fatty acid derivative; benzalkonium chloride; benzethonium chloride, and the like.

Examples of the amphoteric surfactant that may be used may include: imidazoline-based amphoteric surfactant (such as sodium 2-undecyl-N,N,N-(hydroxyethylcarboxymethyl)-2-imidazoline and 2-cocoyl-2-imidazolinium hydroxide-1-carboxyethyloxy disodium salt); and betaine-based surfactant (such as 2-heptadecyl-N-carboxymethyl-N-hydroxyethyl imidazolinium betaine, lauryl dimethylaminoacetic acid betaine, alkyl betaine, amidobetaine, and sulfobetaine).

Examples of the lipophilic nonionic surfactants may include sorbitan fatty acid ester (such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2 ethylhexylate, diglycerol sorbitan tetra-2 ethylhexylate, etc); glyceryl polyglyceryl fatty acid (such as glyceryl monocotton oil fatty acid, glyceryl monoerucate, glyceryl sesquioleate, glyceryl monostearate, glyceryl α, α'-oleate pyroglutamate, glyceryl monostearate malate, etc); propylene glycol fatty acid ester (such as propylene glycol monostearate, etc); hydrogenated caster oil derivative; glyceryl alkyl ether, and the like.

Examples of the hydrophilic nonionic surfactants that may be used may include POE sorbitan fatty acid ester (such as POE sorbitan monooleate, POE sorbitan monostearate, POE sorbitan monooleate, POE sorbitan tetraoleate); POE sorbit fatty acid ester (such as POE sorbit monolaurate, POE sorbit monooleate, POE sorbit pentaoleate, POE sorbit monostearate), POE glyceryl fatty acid ester (such as POE monooleate such as POE glyceryl monostearate, POE glyceryl monoisostearate, POE glyceryl triisostearate); POE fatty acid ester (such as POE distearate, POE monodioleate, ethyleneglycol distearate); POE alkyl ether (such as POE lauryl ether, POE oleyl ether, POE stearyl ether, POE behenyl ether, POE-2-octyldodecyl ether, POE cholestanol ether); puluronic type (such as Puluronic), POE/POP alkyl ethers (such as POE/POP cetyl ether, POE/POP 2-decyltetradecyl ether, POE/POP monobutyl ether, POE/POP hydrogenated lanoline, POE/POP glycerin ether); tetra POE/tetra POP ethylenediamine condensation products (such as Tetronic); POE castor oil hydrogenated castor oil derivative (such as POE caster oil, POE hydrogenated caster oil, POE hydrogenated caster oil monoisostearate, POE hydrogenated castor oil triisostearate, POE hydrogenated caster oil monopyroglutamate monoisostearate diester, POE hydrogenated oil maleate); POE beeswax/lanoline derivative (such as POE sorbitol beeswax); alkanolamide (such as coconut oil fatty acid diethanolamide, lauric acid monoethanolamide, fatty acid isopropanolamide); POE propyleneglycol fatty acid ester; POE alkyl amines; POE fatty acid amide; sucrose fatty acid ester; alkylethoxydimethylamine oxide; trioleyl phosphoric acid and the like.

The surface-tension lowering agent in the ink composition of the present disclosure can be added until the surface-tension of the ink composition becomes the surface-tension as desired. The content of the surface-tension lowering agent is preferably 5% by mass or greater, and more preferably 8% by mass or greater with respect to the mass of the ink composition, for example. If the content of the surface-tension lowering agent is smaller than 5% by mass, dispensability will deteriorate. The content of the surface-tension lowereing agent can be 10% by mass or greater, 15% by mass or greater, or 20% by mass or greater with respect to the mass of the ink composition, for example. The content of the surface-tension lowering agent is preferably 30% by mass or smaller, and more preferably 25% by mass or smaller with respect to the mass of the ink composition, for example. If the content of the surface-tension lowering agent exceeds 30% by mass, dispersibility of the pigment will deteriorate.

[Other Components]

The ink composition of the present disclosure may include, as appropriate and as necessary, other components within the range of not inhibiting the effect of the present disclosure such as esters, moisturizers, water-soluble polymers, thickeners, film-forming agents, ultraviolet light absorbers, sequestrants, amino acids, organic amines, polymeric emulsions, pH adjusters, skin nutrients, vitamins, antioxidants, antioxidant aids, perfumes, water and the like.

Examples of other components that can be blended are listed in the following. At least one of the components listed below may be added to the ink composition of the present disclosure.

Examples of the moisturizers may include polyethylene glycol, propylene glycol, glycerin, 1,3-butylene glycol, xylitol, sorbitol, maltitol, chondroitin sulfate, hyaluronic acid, mucoitin sulfate, charonic acid, atelocollagen, cholesteryl 12-hydroxystearate, sodium lactate, bile salt, dl-pyrrolidone carboxylate, alkyleneoxide derivative, short-chain soluble collagen, diglycerin (EO)PO adduct, chestnut rose extract, yarrow extract, melilot extract, and the like.

Examples of the natural water-soluble polymer may include plant-based polymer (such as gum Arabic, gum tragacanth, galactan, guar gum, locust bean gum, gum karaya, carrageenan, pectine, agar, quince seed (*Cydonia oblonga*), algae colloid (brown algae extract), starch (rice, corn, potato, wheat), glicyrrhizic acid); microorganism based polymer (such as xanthan gum, dextran, succinoglycan, pullulan, etc), animal-based polymer (such as collagen, casein, albumin, gelatine, etc) and the like.

Examples of the semisynthetic water-soluble polymer may include starch-based polymer (such as carboxymethyl starch, methylhydroxypropyl starch, etc); cellulose-based polymer (such as methylcellulose, ethylcellulose, methylhydroxypropylcellulose, hydroxyethylcellulose, cellulose sodium sulfate, hydroxypropylcellulose, carboxymethylcellulose, sodium calboxymethyl cellulose, crystalline cellulose, cellulose powder, etc); algin acid-based polymer (such as sodium alginate, propylene glycol alginate ester, etc), and the like.

Examples of the synthetic water-soluble polymer may include vinyl based polymer (such as polyvinyl alcohol, polyvinyl methyl ether, polyvinylpyrrolidone, carboxyvinylpolymer, etc); polyoxyethylene based polymer (such as polyoxyethylenepolyoxypropylene copolymer such as polyethylene glycol 20,000, 40,000 and 60,000, etc); acrylic polymer (such as sodium polyacrylate, polyethylacrylate, polyacrylamide, etc); polyethyleneimine; cationic polymer; and the like.

Examples of the thickeners may include gum arabic, carrageenan, karaya gum, tragacanth gum, carob gum, quince seed (marmelo), casein, dextrin, gelatin, sodium pectate, sodium alginate, methyl cellulose, ethyl cellulose, carboxymethyl cellulose (CMC), hydroxyethyl cellulose, hydroxypropyl cellulose, polyvinyl alcohol (PVA), polyvinylmethyl ether (PVM), PVP (polyvinyl pyrrolidone), polysodium acrylate, carboxyvinyl polymer, locust bean gum, guar gum, tamarind gum, dialkyldimethylammonium sulfate cellulose, xanthan gum, aluminum magnesium silicate, bentonite, hectorite, aluminum magnesium silicate (Veegum), sodium magnesium silicate (Laponite), silicic acid anhydride gellan gum, and *Tremella fuciformis* polysaccharide.

Examples of the film-forming agent may include an anionic film-forming agent (such as (meta)acrylic acid/(meta)acrylic acid ester copolymer, methyl vinyl ether/maleic anhydride copolymer, etc), a cationic film-forming agent (such as cationic cellulose, diallyldimethylammonium chloride polymer, diallyldimethylammonium chloride/acrylic amide copolymer, etc), a nonionc film-forming agent (such as polyvinyl alcohol, polyvinylpyrrolidone, polyvinyl acetate, polyacrylic ester copolymer, (meta)acrylamide, polymeric silicone, silicone resin, trimethylsiloxysilicate, etc), and the like.

Examples of the ultraviolet light absorbers may include benzoic acid family ultraviolet light absorber (such as p-aminobenzoic acid (hereinafter abbreviated as PABA), PABA monoglycerine ester, N,N-dipropoxy PABA ethyl ester, N,N-diethoxy PABA ethyl ester, N,N-dimethyl PABA ethyl ester, N,N-dimethyl PABA butyl ester, N,N-dimethyl PABA ethyl ester, etc); anthranilic acid family ultraviolet light absorber (such as homomenthyl N-acetylanthranilate etc); salicylic acid family ultraviolet light absorber (such as amyl salicylate, menthyl salicylate, homomenthyl salicylate, octyl salicylate, phenyl salicylate, benzyl salicylate, p-isopropanolphenyl salicylate, etc); cinnamic acid family ultraviolet light absorber (such as octyl methoxycinnamate, ethyl 4-isopropylcinnamate, methyl 2,5-diisopropylcinnamate, ethyl 2,4-diisopropylcinnamate, methyl 2,4-di isopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate, glyceryl mono-2-ethylhexanoyl-diparamethoxycinnamate, etc); benzophenone family ultraviolet light absorber (such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, 4-hydroxy-3-carboxybenzophenone, etc); 3-(4'-methylbenzyl idene)-d,l-camphor and 3-benzyl idene-d,l-camphor; 2-phenyl-5-methylbenzoxazol; 2,2'-hydroxy-5-methylphenylbenzotriazol, 2-(2'-hydroxy-5'-t-octylphenyl) benzotriazol, 2-(2'-hydroxy-5'-methylphenylbenzotriazol; dibenzalazine; dianisoylmethane; 4-methoxy-4'-t-butyldibenzoylmethane; 5-(3,3-dimethyl-2-norbornylidene)-3-pentane-2-one; dimorpholinopyridazinone; 2-ethylhexyl 2-cyano-3,3-diphenylacrylate; 2,4-bis-{[4-(2-ethylhexyloxy)-2-hydroxy]-phenyl}-6-(4-methoxyphenyl)-(1,3,5)-triazine, and the like.

Examples of the sequestrant may include 1-hydroxyethane-1, 1-diphosphonic acid, 1-hydroxyethane, 1-diphosphonic acid 4Na salt, disodium edetate, trisodium edetate, tetrasodium edetate, sodium citrate, sodium polyphosphate, sodium metaphosphate, gluconic acid, phosphoric acid, citric acid, ascorbic acid, succinic acid, edetic acid, trisodium hydroxyethyl ethylenediamine triacetate, and the like.

Examples of the amino acid may include neutral amino acid (such as threonine, cysteine, etc); basic amino acid (such as hydroxylysine, etc) and the like. Examples of the amino acid derivative may include sodium acyl sarcosinate (sodium lauroyl sarcosinate), acyl glutamate, sodium acyl β-alanine, glutathione, pyrrolidone carboxylate, and the like.

Examples of the organic amine may include monoethanolamine, diethanolamine, triethanolamine, morpholine, triisopropanolamine, 2-amino-2-methyl-1,3-propanediol, 2-amino-2-methyl-1-propanol, and the like.

Examples of the polymer emulsion may include acrylic resin emulsion, ethyl polyacrylate emulsion, solution of acrylic resin, polyacrylalkylester emulsion, polyvinyl acetate resin emulsion, natural rubber latex, and the like.

Examples of the pH modifier may include buffer such as lactic acid-sodium lactate, citric acid-sodium citrate, succinic acid-sodium succinate, and the like.

Examples of the vitamins may include vitamins A, B1, B2, B6, C, E and derivatives thereof, pantothenic acid and derivatives thereof, biotin, and the like.

Examples of the anti-oxidant may include tocopherols, dibutyl hydroxy toluene, butyl hydroxy anisole, and gallic acid esters, and the like.

Examples of the anti-oxidant aid may include phosphoric acid, citric acid, ascorbic acid, maleic acid, malonic acid, succinic acid, fumaric acid, cephalin, hexamethaphosphate, phytic acid, ethylenediaminetetraacetic acid, and the like.

Examples of other containable compositions may include an antiseptic agent (such as ethylparaben, butylparaben, chlorphenesin, 2-phenoxyethanol, etc); antiphlogistic (such as glycyrrhizinic acid derivatives, glycyrrhetic acid derivatives, salicylic acid derivatives, hinokitiol, zinc oxide, allantoin, etc); a skin-whitening agent (such as placental extract, saxifrage extract, arbutin, etc); various extracts (such as phellodendron bark (cork tree bark), coptis rhizome, lithospermum, peony, swertia herb, birch, sage, loquat, carrot, aloe, mallow, iris, grape, Coix seed, sponge gourd, lily, saffron, cnidium rhizome, ginger, Hypericum, restharrow, garlic, red pepper, citrus unshiu, Japanese Angelica, seaweed, etc); an activator (such as royal jelly, photosensitzer, cholesterol derivatives, etc); a blood circulation promotion agent (such as nonylic acid vanillylamide, nicotine acid benzyl ester, nicotine acid β-butoxyethyl ester, capsaicin, zingerone, cantharides tincture, ichthammol, tannic acid, α-borneol, tocopheryl nicotinate, meso-inositol hexanicotinate, cyclandelate, cinnarizine, tolazoline, acetylcholine, verapamil, cepharanthine, γ-oryzanol, etc); an antiseborrheric agent, (such as sulfur, thianthl, etc); an anti-inflammatory agent (such as tranexamic acid, thiotaurine, hypotaurine, etc), and the like.

The composition of the present disclosure further may include, as necessary, caffeine, tannin, verapamil, tranexamic acid and derivatives thereof; various crude drug extracts such as licorice, Chinese quince, Pyrola japonica and the like; drugs such as tocopherol acetate, glycyrrhetinic acid, glycyrrhizic acid and derivatives thereof, or salts thereof; skin-whitening agents such as vitamin C, magnesium ascorbyl phosphate, ascorbic acid glucoside, arbutin, kojic acid and the like; amino acids such as arginine and lysine and the like and derivatives thereof.

[Dispersion Mechanism]

FIG. 1 is a schematic view showing a dispersed state of pigment 1 in the ink composition of the present disclosure. In the ink composition of the present disclosure, it is considered that pigment 1 is dispersed as shown in FIG. 1. In the solvent, the surface of pigment 1 bears a first charge (a positive charge in FIG. 1). Ionic polymer 2 is ionized in the solvent and bears a second charge (a negative charge in FIG. 1). It is considered that polymeric ions gather near the surface of pigment 1 to maintain electrical neutrality. In the solvent, it is considered that ionic polymer 2 is electrostatically and/or ionically bonded to the surface of pigment 1. Alternatively, it is considered that ionic polymer 2 is attached or adsorbed to the surface of pigment 1. Accordingly, it is considered that pigment 1 and ionic polymer 2 form a complex. It is considered that a plurality of ionic polymers 2 are bonded or attached to one primary particle and/or secondary particle of pigment 1. It is considered that, in the complex, a polymer chain of ionic polymer 2 is not contracted around pigment 1 and is stretched outward from pigment 1.

The average particle size of the complex may be 200 nm or greater. Moreover, the average particle size of the complex may be 800 nm or smaller. The average particle size of the complex can be measured in accordance with a dynamic light scattering method. The polydispersity index (PDI) of the complex is preferably 0.2 or smaller. The polydispersity index can be calculated by particle size distribution measured in accordance with a dynamic light scattering method.

It is considered that polyvalent ion 3 bearing the first charge is electrostatically and/or ionically bonded to ionic polymer 2 bearing the second charge in the solvent. Moreover, it is considered that polyvalent ion 3 is electrostatically and/or ionically bonded to ionic polymer 2 adsorbed to another pigment 1. Accordingly, it is considered that polyvalent ion 3 has a structure so as to crosslink ionic polymers 2 and/or the complexes. That is, it is considered that pigment 1, ionic polymer 2 and polyvalent ion 3 form a network by weak ionic bond or ionic interaction. It is considered that pigment 1 weakly flocculates via ionic polymer 2 and polyvalent ion 3. Furthermore, it is considered that the network and/or weak flocculation suppresses sedimentation of pigment 1 and suppresses solidification even if pigment 1 sediments. Moreover, it is considered that the network and/or weak flocculation make(s) it easy that pigment 1 after being left to stand is reflowed and redispersed by external force such as shaking since the network and/or weak flocculation can be easily decomposed by the external force. In FIG. 1, the polyvalent ion is shown as a divalent ion, but it is not limited thereto.

[Surface-Tension]

The surface-tension, which is measured by Wilhelmy method, of the ink composition of the present disclosure is preferably 55 mN/m or smaller, more preferably 53 mN/m or smaller, more preferably 52.5 mN/m or smaller, more preferably 52 mN/m or smaller, more preferably 51.5 mN/m or smaller, more preferably 51 mN/m or smaller, more preferably 50.5 mN/m or smaller, more preferably 50 mN/m or smaller, more preferably 49.5 mN/m or smaller, and further more preferably 49 mN/m or smaller. Ink-jet dispensing becomes possible by lowering the surface-tension.

[Viscosity]

The viscosity at a shear velocity of 100 s$^{-1}$ or greater of the ink composition of the present disclosure is preferably 50 mPa·s or smaller, preferably 40 mPa·s or smaller, more preferably 30 mPa·s or smaller, more preferably 25 mPa·s or smaller, more preferably 20 mPa·s or smaller, more preferably 15 mPa·s or smaller, and further more preferably 10 mPa·s or smaller. If the viscosity at a shear velocity of 100 s$^{-1}$ or greater exceeds 50 mPa·s, ink-jet dispensing becomes difficult.

The viscosity at a shear velocity of 1 s$^{-1}$ of the ink composition of the present disclosure is preferably 800 mPa·s or smaller, more preferably 500 mPa·s or smaller, more preferably 300 mPa·s or smaller, more preferably 200 mPa·s or smaller, and further more preferably 100 mPa·s or smaller. If the viscosity at a shear velocity of 1 s$^{-1}$ exceeds 800 mPa·s, ink-jet dispensing becomes difficult.

The viscosity of the ink composition of the present disclosure can be measured by a rheometer.

[pH]

It is preferred that the pH of the ink composition of the present disclosure is appropriately adjusted so as to achieve a desired viscosity.

In the ink composition of the present disclosure, sedimentation and aggregation of the pigment are suppressed. Accordingly, the ink composition can be stably dispensed even when the ink composition is used in ink-jet applications.

Even powders which tend to sediment and flocculate easily, such as titanium oxide and the like, can be used as the pigment in the composition of the present disclosure. Accordingly, an ink for ink-jet applications having a desired color (white, for example) can be achieved.

Even when a white-based pigment such as titanium oxide and the like is used, the ink composition of the present disclosure can have a high concealing ability since the particle size of the pigment is suitably large.

A method of producing of the ink composition of the present disclosure is described as a second embodiment. The method described below is merely an example, and the production method is not limited thereto. Reference should be made to the aforementioned description for details of each component.

First of all, the first powder of which the surface is to be charged with the first charge in the solvent is added to the solvent (a first addition step). The surface of the first powder is charged if necessary (a charging step). For example, pH may be adjusted. Alternatively, the surface of the powder may be charged by adding a charging agent to the solvent. For example, cationic polymers such as polyethylene imine and the like can be added when the surface of the powder needs to be charged positively.

Next, a polyelectrolyte that generates the ionic polymer bearing the second charge is added to the solvent to prepare a first mixture solution (a second addition step). Accordingly, it is considered that the ionic polymer generated by electrolytic dissociation of the polyelectrolyte electrically adsorbs to the surface of the first powder.

With respect to the order of addition of the first powder and the polyelectrolyte, it is preferred that addition of the first powder is first. The ionic polymer can be adsorbed to the first powder easily by adding the ionic polymer in a state where the first powder is dispersed in advance.

A process for loosening contraction of the polymer chain of the ionic polymer may be performed (a loosening step). For example, stress and/or strain, such as pressure, may be applied to the liquid so that entanglement of the polymer chain may be disentangled and the polymer chain may stretch outward from the particle to which the polymer chain is adsorbed. The application time of pressure to the liquid is preferably one hour or longer so that loosening of the polymer chain may be advanced sufficiently. For example, contraction of the polymer chain can be loosened by applying pressure to the liquid and then sealing the container in which the liquid is contained.

When a powder other than the first powder, e.g. a second powder, is added, the powder can be added in either the first addition step or the second step. Or, separately from the first mixture solution, each steps as stated above may be performed to the second powder to prepare a second mixture solution. Then, the first mixture solution including the first powder and the second mixture solution including the second powder can be mixed to prepare a mixture solution including the first powder and the second powder.

Next, a compound (a salt, for example) that generates the polyvalent ion bearing the first charge by electrolytic dissociation, for example, is added to the aforementioned mixture (a third addition step). It is considered that the polyvalent ion generated in the solvent electrostatically and/or conically bonds or weakly bonds with the ionic polymer. Accordingly, it is considered that the pigment including the first powder and/or the second powder weakly flocculates via the ionic polymer and the polyvalent ion.

The addition rate of each component can be determined in accordance with the aforementioned contents.

Other components can be added in each step so that the effect of the present disclosure is not inhibited.

According to the second embodiment, the ink composition of the present disclosure according to the first embodiment can be prepared easily. In cases where the pigment, the ionic polymer and the polyvalent ion are added simultaneously, it is considered that polymer chain of the ionic polymer adsorbed to the powder contracts. Accordingly, the polyvalent ion cannot connect the ionic polymers; as a result, a network is not formed and the powder cannot form weak flocculation. On the other hand, according to the method of the present disclosure, it is considered that the polymer chain of the ionic polymer adsorbed to the pigment can be stretched. Accordingly, the polyvalent ion can connect the ionic polymers; as a result, a network is formed and the pigment can form weak flocculation.

An ink cartridge of the present disclosure according to a third embodiment will be described. The ink cartridge can be used for ink-jet applications. An ink-jet ink cartridge may be of a thermal type or a piezo type.

Figure 2:
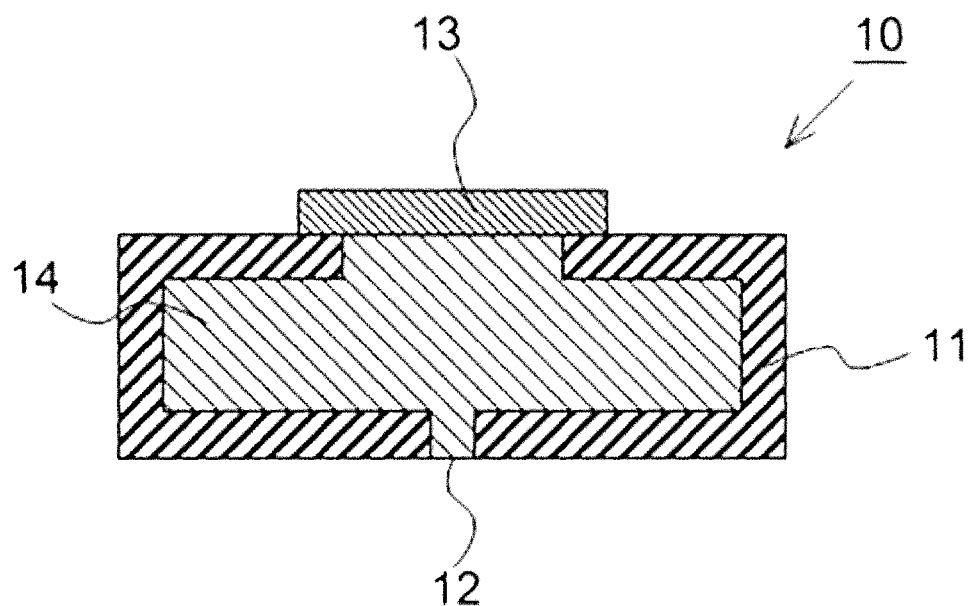
FIG. 2 is a schematic cross-sectional view of the ink cartridge.
Figure 3:
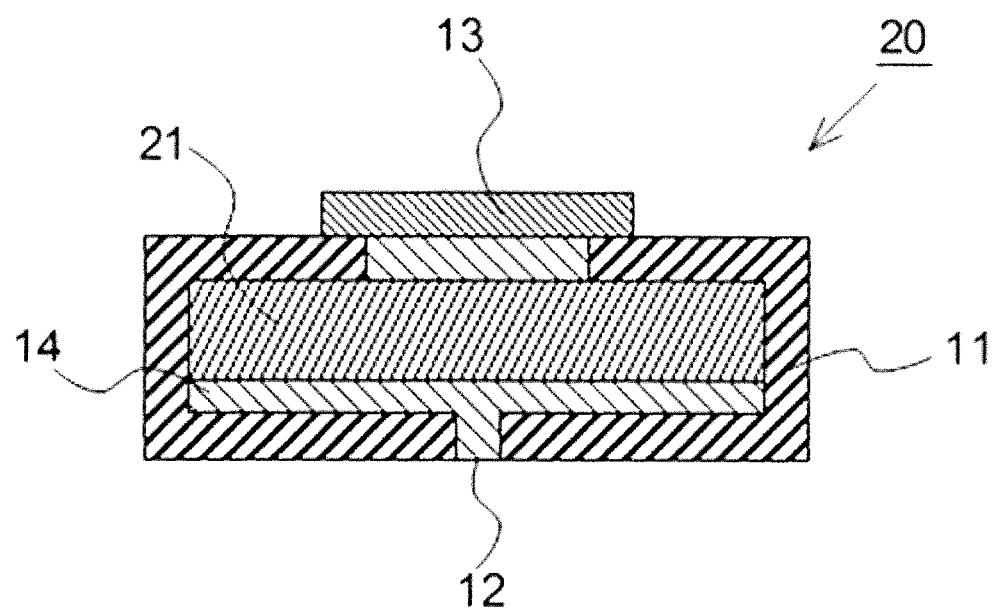
FIG. 3 is a schematic cross-sectional view of the ink cartridge.

FIG. 2 shows a schematic cross-sectional view of one mode of the ink cartridge for ink-jet applications. Ink cartridge 10 comprises ink chamber 11, dispensing element 13, and ink 14 including the ink composition according to the first embodiment. Ink chamber 11 comprises dispensing outlet 12 for dispensing ink 14. Dispensing element 13 is an element to dispense droplets of ink 14 from dispensing outlet 12. In thermal ink-jet applications, dispensing element 13 may be a heater, for example. In piezo ink-jet applications, dispensing element 13 may be a piezo element and a diaphragm, for example FIG. 3 shows a schematic cross-sectional view of the ink cartridge for ink-jet applications having a mode different from FIG. 2. Ink cartridge 20 can further comprise ink absorber 21 that absorbs and stores ink 14 in ink chamber 11. Porous bodies such as fibers, sponges and the like can be used as ink absorber 21.

The ink-jet cartridge according to the third embodiment can use the ink composition according to the first embodiment as the ink. According to the ink composition of the first embodiment, the ink composition can be stably dispensed even when the ink absorber is present.

The ink-jet cartridge according to the third embodiment can be used in printers, cosmetic devices and the like, for example.

A cosmetic device of the present disclosure according to a fourth embodiment will be described. The cosmetic device is a device for dispensing the ink composition according to the first embodiment to skin. The cosmetic device can comprise the ink cartridge according to the third embodiment. The ink cartridge may be configured detachably to the cosmetic device. Depending on a purpose, the ink composition according to the first embodiment to be dispensed can be applied to skin external agents, cosmetics, cosmeceuticals and the like. The cosmetic device can be a portable type that can be carried around easily.

According to the cosmetic device of the fourth embodiment, the ink composition according to the first embodiment can be applied to skin with pinpoint accuracy. By using the ink composition according to the first embodiment, cosmetics having a color depending on the purpose, such as skin color and the like, can be applied.

EXAMPLES

The ink composition of the present disclosure will be described with examples hereinbelow. The ink composition of the present disclosure, however, is not limited to the following examples. Contents shown in the following tables are shown by "% by mass".

Test Examples 1 to 5

A white-based ink composition was prepared to test whether the composition is able to be dispensed by an ink-jet method. As the white-based pigment, at least one of zinc oxide and titanium oxide was used. It is considered that the surfaces of zinc oxide and titanium oxide are positively charged in water. Having Test example 1 as an example, a production method of a white-based ink composition will be described. First of all, a zinc oxide powder and sodium polyacrylate were added to an ion-exchanged water, and the zinc oxide powder was dispersed with an ultrasonic vibration to prepare a first pigment dispersion. Likewise, Titanium oxide A powder and sodium polyacrylate were added to an ion-exchanged water separately, and Titanium oxide A powder was dispersed with an ultrasonic vibration to prepare a second pigment dispersion. A polyacrylate ion generated from sodium polyacrylate corresponds to the above-mentioned ionic polymer. Next, in order to achieve a desired content of the white-based pigment, the first dispersion and the second dispersion were added to an ion-exchanged water and mixed to give a mixed solution, and then magnesium chloride was added to the mixed solution. A magnesium ion generated from magnesium chloride corresponds to the above-mentioned polyvalent ion. Next, in order to achieve desired surface-tension and viscosity, dipropylene glycol, which is a surface-tension lowering agent, and a citric acid, which is a pH adjuster, were added to prepare an ink composition. The ink compositions of Test examples 2 to 5 were prepared in the same manner. The prepared ink compositions were observed to be white.

Titanium oxide A corresponds to the above-mentioned first powder. Zinc oxide corresponds to the above-mentioned second powder. Table 1 shows the average particle sizes of zinc oxide and titanium oxide in the ink composition. The catalogue value as used in Table 1 is an average particle size of the primary particles published by the manufacturer of the powder. The measurement value after dispersion treatment as used in Table 1 is a measurement value of the powder subjected to an ultrasonic vibration and dispersed in the solvent. The catalogue value of the primary particles of zinc oxide was 30 nm to 60 nm, but the average particle size in the ink composition after dispersion treatment was 100 nm to 200 nm. The primary particle of Titanium oxide A powder is spherical. The catalogue value of the primary particles of Titanium oxide A was 200 nm, but the average particle size in the ink composition after dispersion treatment was 200 nm to 300 nm. The catalogue value of the primary particles of Titanium oxide B was 10 nm to 20 nm, but the average particle size in the ink composition after dispersion treatment was 150 nm to 200 nm. There is no big difference between the measurement value after dispersion treatment of the average particle size of Titanium oxide A and the catalogue value, and thus it is considered that aggregation (secondary particle) in Titanium oxide A is less. Therefore, it is considered that the particle shape in Titanium oxide A is mainly spherical. On the other hand, in zinc oxide and Titanium oxide B, there are big differences between the measurement values after dispersion treatment and the catalogue values, and thus it is considered that numerous secondary particles exist in zinc oxide and Titanium oxide B. Therefore, it is considered that the particle shapes in zinc oxide and Titanium oxide B are mainly non-spherical or indefinite-shaped.

TABLE 1

| | Average particle size (nm) | |
|---|---|---|
| | Catalogue value | Measurement value after dispersion treatment |
| Zinc oxide | 30-60 | 100-200 |
| Titanium oxide A | 200 | 200-300 |
| Titanium oxide B | 10-20 | 150-250 |

The viscosity at shear velocities of 1 $s^{-1}$ and 100 $s^{-1}$, and the surface-tension of the prepared ink composition were measured. The viscosity was measured by a rheometer. As for the surface-tension, a sample after one month from the preparation of the ink composition was measured by a Wilhelmy method.

The prepared ink composition was filled to a thermal ink-jet cartridge comprising an ink absorber in an ink tank to test whether it can be printed on a black paper. The evaluation criteria are shown below. A test for an ability to be dispensed was performed on the day when the ink composition was filled to the ink cartridge and the next day.
[Ability to be Dispensed]
A: White colored letters could be printed by the ink-jet method.
B: White colored letters could not be printed by the ink-jet method.

The formulations and the measurement results are shown in Table 2. Usually, the white-based pigment such as titanium oxide has a large specific gravity, so that it tends to sediment and aggregate easily. Accordingly, so far, it had been difficult to use the white-based pigment for printing by the ink-jet method. In particular, it had been difficult to redispere the pigment once sedimentation and aggregation occurs in the ink cartridge comprising the ink absorber. In the ink compositions according to Test examples 1 to 5, however, a stable ink-jet dispensing was possible, and it was confirmed that white-colored letters can be printed clearly. In the ink composition of the present disclosure, dispersibility of the pigment powder is enhanced by the ionic polymer and the polyvalent ion, and aggregation is suppressed at the same time. Accordingly, it is considered that the ink composition of the present disclosure could be used for printing by the ink-jet method. Moreover, it is found that the ink composition of the present disclosure could be used for printing on the next day when the ink composition was filled to the ink cartridge, and it was confirmed that the printable state is not temporary. Furthermore, it is found that the ink composition of the present disclosure is also applicable to the ink-jet cartridge comprising the ink absorber.

Moreover, according to visual observation, the printed letters were high in concealing ability. In Test examples 1 to 5, it is considered that concealing ability was enhanced by using the titanium oxide powder having a relatively large particle size. It is confirmed that the ink composition with Titanium oxide A alone could be dispensed in Test example 4 and 5, but the ink composition could be also dispensed by combining zinc oxide particles with Titanium oxide A in Test examples 1 to 3. It is considered that concealing ability was further able to be enhanced by combining pigments having different sizes and/or pigments of different types. Moreover, it is considered that aggregation of the pigment is suppressed by combining powders of different types.

TABLE 2

| Test Example | | 1 | 2 | 3 | 4 | 5 |
|---|---|---|---|---|---|---|
| Zinc oxide | | 5.0 | 2.4 | 2.4 | — | — |
| Titanium oxide A | | 10 | 10 | 12.4 | 15.1 | 10.0 |
| Titanium oxide B | | — | — | — | — | — |
| Sodium polyacrylate | | 0.3 | 0.2 | 0.3 | 0.3 | 0.2 |
| Magnesium chloride | | 0.1 | 0.1 | 0.1 | 0.1 | 0.2 |
| Dipropylene glycol | | 19.9 | 20.4 | 22.8 | 23.1 | 18.0 |
| Citric acid | | 0.3 | 0.2 | 0.2 | 0.1 | 0.1 |
| Ion exchanged water | | Balance | Balance | Balance | Balance | Balance |
| Total | | 100 | 100 | 100 | 100 | 100 |
| Viscosity | $1\ s^{-1}$ | 25 | 100 | 210 | 12 | 20 |
| (mPa · s) | $100\ s^{-1}$ | 5 | 6 | 8 | 3 | 5 |
| Ability to | The day | A | A | A | A | A |
| be dispensed | Next day | A | A | A | A | A |

Test Examples 6 to 9

Ink compositions having formulations different from Test examples 1 to 5 were prepared to perform the same tests as in Test examples 1 to 5. In Test examples 6 and 7, combinations of zinc oxide and Titanium oxide A were used as the pigment powder. In Test examples 8 and 9, combinations of zinc oxide and Titanium oxide B were used as the pigment powder. Moreover, in Test examples 6 and 8, the content of diprolylene glycol, which is the surface-tension lowering agent, is made high so that the surface-tension becomes lower. The preparation method and the test method in Test examples 6 to 9 are the same as in Test examples 1 to 5. The formulations and results are shown in Table 3.

In Test example 6, the ink composition could be dispensed by ink-jet like in Test examples 1 to 5. In Test examples 7 to 9, however, the ink compositions were not able to be dispensed by ink-jet.

When Test examples 6 and 7 are compared, the content of diprolylene glycol is lower in Test example 7, and thus the surface-tension is higher. Therefore, it is considered that ink-jet dispensing became difficult due to the high surface-tension. Accordingly, it is considered that the surface-tension of the ink composition is preferably 53 mN/m or smaller, preferably 52 mN/m or smaller, more preferably 51 mN/n or smaller, and more preferably 50 mN/m or smaller.

In Test examples 8 and 9, Titanium oxide B is added instead of Titanium oxide A. In Test example 8, ink-jet dispensing was impossible even when the surface-tension was 52 mN/m or smaller. Accordingly, it is considered that ink-jet dispensing became impossible by at least one reason among: the average particle size of a part of the pigment; aggregation of the pigment particles; the shape of the pigment particle; and the like. In particular, it is considered that the main shape of the pigment particle is preferably spherical.

TABLE 3

| Test Example | | 6 | 7 | 8 | 9 |
|---|---|---|---|---|---|
| Zinc oxide | | 10 | 10 | 10 | 10 |
| Titanium oxide A | | 10 | 10 | — | — |
| Titanium oxide B | | — | — | 10 | 10 |
| Sodium polyacrylate | | 0.4 | 0.4 | 0.4 | 0.4 |
| Magnesium chloride | | 0.1 | 0.1 | 0.1 | 0.1 |
| Dipropylene glycol | | 10 | 6.6 | 10 | 6.6 |
| Citric acid | | 0.3 | 0.3 | 0.4 | 0.4 |
| Ion exchanged water | | Balance | Balance | Balance | Balance |
| Total | | 100 | 100 | 100 | 100 |
| Viscosity | $1\ s^{-1}$ | 52 | 18 | 44 | 5 |
| (mPa · s) | $100\ s^{-1}$ | 15 | 9 | 21 | 5 |
| Surface-tension (mN/m) | | 48.1 | 53.2 | 47.9 | 53.6 |
| Ability to be dispensed | The day | A | B | B | B |

Test Examples 10 to 13

To prepare the ink compositions, a combination of zinc oxide and Titanium oxide A was used as the pigment powder in Test example 10, and combinations of Titanium oxide A and Titanium oxide B were used as the pigment powder in Test examples 11 to 13, and the same tests as in Test examples 1 to 5 were performed. The preparation method and the test method in Test examples 10 to 13 are the same as in Test examples 1 to 5. The formulations and the results are shown in Table 4.

Other than the content of diprolylene glycol, Test example 10 is the same as Test example 1, and there was no problem in the ability to be dispensed. In Test examples 11 to 13, the ink compositions were able to be dispensed on the day of filling; however, a problem in the ability to be dispensed arose at least on the next day of filing.

In Test example 11, the content of Titanium oxide B, which is considered to be non-spherical or indefinite-shaped, is higher than in Test examples 10, 12 and 13. It is considered that the problem in the ability to be dispensed arose in Test example 11 because: there were many secondary particles (many non-spherical particles or indefinite-shaped particles); and/or the viscosity became high. Accordingly, it is considered that the content of the second powder is preferably 45% by mass or smaller, more preferably 40% by mass or smaller, more preferably 35% by mass or smaller, and more preferably 30% by mass with respect to the total mass of the powder (pigment). As shown in Test examples 4 and 5, the second powder may not be added.

In Test examples 12 and 13, there was no problem in the ability to be dispensed of the day of filling, but a problem in the ability to be dispensed of the next day of filling arose. Since the problem in the ability to be dispensed of the next day of filling did not arise in Test example 10 having a similar formulation, it is considered that the ability to be dispensed was affected by the first powder and the second powder being the same type. For example, it is considered that since the powders of the same type have high affinity to each other, the number of aggregations formed became larger as the time passes, and thus the ability to be dispensed was deteriorated. Therefore, in order to enhance stability over a long term, it is considered that the first powder and the second powder are preferably of different types.

From Test examples 1 to 13 together, it is considered that the droplet becomes smaller as the viscosity, in particular the viscosity at a shear velocity of $100\ s^{-1}$, is lower, and thus ink-jet-dispensing ability can be enhanced. Therefore, it is considered that the viscosity at a shear velocity of $1\ s^{-1}$ is preferably 800 mPa·s or smaller, more preferably 500 mPa·s or smaller, more preferably 300 mPa·s or smaller, more preferably 200 mPa·s or smaller, and further more preferably 100 mPa·s or smaller. Furthermore, it is considered that the viscosity at a shear velocity of 100 s$^{-1}$ is preferably 50 mPa·s or smaller, more preferably 40 mPa·s or smaller, more preferably 30 mPa·s or smaller, more preferably 25 mPa·s or smaller, more preferably 20 mPa·s or smaller, more preferably 15 mPa·s or smaller, and further more preferably 10 mPa·s or smaller.

TABLE 4

| Test Example | | 10 | 11 | 12 | 13 |
|---|---|---|---|---|---|
| Zinc oxide | | 5.0 | — | — | — |
| Titanium oxide A | | 10 | 10 | 10 | 10 |
| Titanium oxide B | | — | 10 | 5.0 | 5.0 |
| Sodium polyacrylate | | 0.3 | 0.4 | 0.3 | 0.3 |
| Magnesium chloride | | 0.1 | 0.1 | 0.1 | 0.1 |
| Dipropylene glycol | | 12.5 | 15.2 | 12.0 | 9.5 |
| Citric acid | | 0.3 | 0.2 | 0.2 | 0.2 |
| Ion exchanged water | | Balance | Balance | Balance | Balance |
| Total | | 100 | 100 | 100 | 100 |
| Viscosity | 1 s$^{-1}$ | 150 | 1000 | 15 | 50 |
| (mPa · s) | 100 s$^{-1}$ | 6 | 50 | 7 | 12 |
| Surface-tension (mN/m) | | 46.8 | 48.3 | 48.3 | 52.3 |
| Ability to be | The day | A | B | A | A |
| dispensed | Next day | A | B | B | B |

Test Examples 14 to 16

In Test examples 14 to 16, the ink compositions were prepared by using the pigment powder of which dispersion treatment by ultrasonic treatment is not performed to at least either one of zinc oxide and titanium oxide, and the same tests as in Test examples 1 to 5 were performed. Other than the point that ultrasonic treatment is not performed, the preparation method and the test method of the ink composition of Test examples 14 to 16 are the same as in Test examples 1 to 5. Table 5 shows the average particle sizes of zinc oxide and titanium oxide in the ink composition. The measurement value without dispersion treatment in Table 5 denotes a measurement value in a state where the powder is dispersed in the solvent without applying ultrasonic vibration. Table 6 shows the formulations and the results. In Table 6, the pigments without being subjected to dispersion treatment by ultrasonic vibration are shown as "zinc oxide without dispersion treatment" and "Titanium oxide A without dispersion treatment", respectively. The pigments subjected to dispersion treatment by ultrasonic vibration are shown as "dispersed zinc oxide" and "dispersed Titanium oxide A", respectively.

The average particle sizes of zinc oxide without dispersion treatment and Titanium oxide A without dispersion treatment were larger than the average particles sizes of dispersed zinc oxide and dispersed Titanium oxide A. Therefore, it is considered that zinc oxide without dispersion treatment and Titanium oxide A without dispersion treatment aggregate, respectively. Accordingly, it is considered that the particle shape of Titanium oxide A is not spherical, but indefinite-shaped.

The problems in the ability to be dispensed arose in any of Test examples 14 to 16. In Test examples 14 and 16, it is considered that one of reasons for the problem in the ability to be dispensed was that the particle shape of Titanium oxide was non-spherical. Furthermore, in Test examples 14 to 16, one of reasons for the problem in the ability to be dispensed was also that the particle size of the pigment became larger and thus sedimentation occurred, or clogging occurred in the ink absorber. If the particle size is the cause, it is considered that the average particle size of the pigment powder is preferably 300 μm or smaller. It is considered that the pigment powder having the average particle size of 300 μm or smaller is preferably 70% by mass or greater, more preferably 80% by mass or greater, more preferably 85% by mass or greater, more preferably 90% by mass or greater, more preferably 95% by mass or greater, and furthermore preferably 100% by mass with respect to the total amount of the pigment powder.

TABLE 5

| | | Particle size (nm) | |
|---|---|---|---|
| | Catalogue value | Measurement value without dispersion treatment | Measurement value after dispersion treatment |
| Zinc oxide | 30-60 | 300-400 | 100-200 |
| Titanium oxide A | 200 | 600-800 | 200-300 |

TABLE 6

| Test Example | 14 | 15 | 16 |
|---|---|---|---|
| Dispersed zinc oxide | 5.0 | — | — |
| Zinc oxide without dispersion treatment | — | 5.0 | 5.0 |
| Dispersed Titanium oxide A | — | 10 | — |
| Titanium oxide A without dispersion treatment | 10 | — | 10 |
| Sodium polyacrylate | 0.3 | 0.3 | 0.3 |
| Magnesium chloride | 0.1 | 0.1 | 0.1 |
| Dipropylene glycol | 9.5 | 9.5 | 9.5 |
| Citric acid | 0.3 | 0.3 | 0.3 |
| Ion exchanged water | Balance | Balance | Balance |
| Total | 100 | 100 | 100 |
| Ability to be dispensed | B | B | B |

The ink composition, ink-jet cartridge and cosmetic device of the present invention have been described according to the foregoing embodiments and examples, but the invention is not limited to the foregoing embodiments and examples and may encompass various transformations, modifications, and improvements made to the various disclosed elements (including elements disclosed in the Claims, Description, and Drawings) within the scope of the invention and according to the fundamental technical idea of the present invention. Further, various combinations, substitutions, and selections of the various disclosed elements are possible within the scope of the claims of the invention.

Further issues, objectives, and embodiments (including modifications) of the present invention are revealed also from the entire disclosure of the invention including the Claims.

The numerical ranges disclosed herein are to be construed in such a manner that arbitrary numerical values and ranges falling within the disclosed ranges are treated as being concretely described herein, even where not specifically stated.

INDUSTRIAL APPLICABILITY

The ink composition of the present disclosure can be applied not only to inks for ink-jet applications, but also to inks for paints, pens, correction pens and the like. Furthermore, the ink composition of the present disclosure can be applied as external agents and cosmetics applied to skin.

The ink composition and the ink-jet cartridge of the present disclosure may be used in forms of an on-demand type or a continuous type. Furthermore, a method for dispensing drops to which the ink composition and the ink-jet cartridge of the present disclosure is applicable may be a thermal method or a piezo method.

LIST OF REFERENCE SYMBOLS

1 Pigment
2 Ionic polymer
3 Polyvalent ion
10, 20 Ink cartridge
11 Ink chamber
12 Dispensing outlet
13 Dispensing element
14 Ink
21 Ink absorber

The invention claimed is:

1. An ink composition for ink jet application, comprising:
a solvent;
a pigment comprising a titanium dioxide powder and a zinc oxide powder bearing a positive charge on a surface thereof in said solvent;
an ionic polymer having an anionic functional group; and
a polyvalent ion bearing said positive charge;
wherein:
the content of said titanium dioxide powder in the pigment is 45% by mass to 90% by mass with respect to the total amount of said pigment;
the content of said zinc oxide powder in the pigment is 10% by mass to 55% by mass with respect to the total amount of said pigment;
said ionic polymer comprises at least either one of a polyacrylate ion and a hexamethaphosphate ion;
said polyvalent ion comprises at least either one of a magnesium ion and a calcium ion;
said pigment forms a weak flocculation via said ionic polymer and said polyvalent ion; and
the surface-tension of the ink composition is 53 mN/m or smaller.

2. The ink composition, according to claim 1, wherein:
said titanium dioxide powder has an average particle size of 150 nm to 350 nm.

3. The ink composition, according to claim 1, wherein:
a primary particle of titanium dioxide powder is spherical.

4. The ink composition, according to claim 1, wherein:
the primary particle of said titanium dioxide powder has an average particle size of 100 nm to 300 nm.

5. The ink composition, according to claim 1, wherein:
a ratio of said titanium dioxide powder with respect to the total amount of said pigment is 40% by mass or greater.

6. The ink composition, according to claim 1, wherein:
said second powder has an average particle size of 50 nm to 300 nm.

7. The ink composition, according to claim 1, wherein:
the content of said pigment is 5% by mass to 25% by mass with respect to the mass of the ink composition.

8. The ink composition, according to claim 1, wherein:
the viscosity at a shear velocity of $100\ s^{-1}$ or greater is 40 mPa·s or smaller.

9. The ink composition, according to claim 1, wherein:
said pigment and said ionic polymer are at least one of electrostatically and ionically bonded with one another; and
said ionic polymer and said polyvalent ion are at least one of electrostatically and ionically bonded with one another.

10. The ink composition, according to claim 1, wherein:
the content of a polyelectrolyte that is a source of said ionic polymer is 0.01 part by mass to 0.2 part by mass with respect to 1 part by mass of said pigment.

11. The ink composition, according to claim 1, wherein:
the content of a salt that is a source of said polyvalent ion is 0.15 part by mass to 2 parts by mass with respect to 1 part by mass of said polyelectrolyte that is the source of said ionic polymer.

* * * * *